US011622899B2

(12) United States Patent
Fanelli et al.

(10) Patent No.: US 11,622,899 B2
(45) Date of Patent: Apr. 11, 2023

(54) MUSCLE TENSION RELIEF DEVICE AND ASSOCIATED METHODS

(71) Applicant: Vive Physical Therapy LLC, Holly Springs, NC (US)

(72) Inventors: Joseph Andrew Fanelli, Cameron, NC (US); Shannon Patty Fanelli, Cameron, NC (US); Kelly Catheryn Rouse, Cameron, NC (US); Christopher Ray Randall, Holly Springs, NC (US)

(73) Assignee: Vive Physical Therapy LLC, Holly Springs, NC (US)

(*) Notice: Subject to any disclaimer, the term of this patent is extended or adjusted under 35 U.S.C. 154(b) by 472 days.

(21) Appl. No.: 16/989,920

(22) Filed: Aug. 11, 2020

(65) Prior Publication Data

US 2022/0047441 A1 Feb. 17, 2022

(51) Int. Cl.

| | |
|---|---|
| ***A61G 13/12*** | (2006.01) |
| ***A61F 5/30*** | (2006.01) |
| ***A61G 13/00*** | (2006.01) |

(52) U.S. Cl.

CPC ......... *A61G 13/009* (2013.01); *A61G 13/123* (2013.01); *A61G 13/126* (2013.01); *A61G 13/1285* (2013.01)

(58) Field of Classification Search

CPC .. A61G 13/009; A61G 13/123; A61G 13/126; A61G 13/1285; A61F 5/024;

(Continued)

(56) References Cited

U.S. PATENT DOCUMENTS

| | | | |
|---|---|---|---|
| 4,848,742 A | 7/1989 | Lindley et al. | |
| 6,735,798 B1 * | 5/2004 | Sekizawa ............ | A47C 17/045 5/640 |

(Continued)

FOREIGN PATENT DOCUMENTS

WO WO 96/33779 A1 10/1996

OTHER PUBLICATIONS

How to Use the Hip Hook' (Koth) Oct. 22, 2019 retrieved from "https://www.youtube.com/watch?v=5_H2NZ-9w5s", entire video cited.

(Continued)

*Primary Examiner* — Camtu T Nguyen

(74) *Attorney, Agent, or Firm* — Nelson Mullins Riley & Scarborough LLP

(57) ABSTRACT

Example muscle tension relief devices are provided herein. A muscle tension relief device includes a first base portion extending in a first plane, a second base portion extending in a second plane, and a muscle engagement feature extending generally upwardly. There is a non-zero angle extending between the first plane and the second plane. The device is configured to engage with and relieve tension in a user's iliacus or psoas muscles. The device can transition from a first position resting on the first base portion to a second position resting on the second base portion to cause the muscle engagement feature to change orientation to apply pressure at the proper position on a user's psoas major muscle. The shape of an upper portion of a body of the device and the muscle engagement feature correspond to the shape of a hand, such as that of a physical therapist.

18 Claims, 16 Drawing Sheets

(58) Field of Classification Search
CPC .. A61F 5/026; A61F 5/028; A61F 5/03; A61F 5/30; A61F 5/32; A61H 7/007; A61H 2201/1284; A61H 2201/0153
See application file for complete search history.

(56) References Cited

U.S. PATENT DOCUMENTS

| | | | | |
|---|---|---|---|---|
| D756,529 | S | 5/2016 | Grant | |
| D823,479 | S | 7/2018 | Mollohan | |
| 10,052,255 | B2 | 8/2018 | Harvel | |
| 10,357,419 | B2 | 7/2019 | Zilkha et al. | |
| D879,989 | S | 3/2020 | Mollohan | |
| 11,134,785 | B1 * | 10/2021 | Smart | A47C 16/02 |
| 2011/0313334 | A1 | 12/2011 | Almeida et al. | |
| 2014/0272850 | A1 | 9/2014 | Knight | |
| 2015/0265871 | A1 | 9/2015 | Patel | |
| 2017/0340510 | A1 | 11/2017 | Spewock et al. | |
| 2020/0390639 | A1 * | 12/2020 | Koth | A61H 7/003 |
| 2021/0077855 | A1 * | 3/2021 | Walko | A61H 19/50 |
| 2021/0236371 | A1 * | 8/2021 | Carr | A61H 1/008 |

OTHER PUBLICATIONS

Nov. 15, 2021 Search Report and Written Opinion issued in International Patent Application No. PCT/US21/44629; 8 pp.
“PSO-RITE;” retrieved Jul. 24, 2020 from https://pso-ritc.com/.
“Hip Hook;” retrieved Jul. 24, 2020 from https://www.christinekoth.com/hip-hook.

* cited by examiner

MUSCLE TENSION RELIEF DEVICE AND ASSOCIATED METHODS

FIELD OF THE INVENTION

Example embodiments of the present invention generally relate to muscle tension relief devices and, more particularly, to muscle tension relief devices capable of providing tension relief for the iliacus, psoas major, or psoas minor muscles.

BACKGROUND

Muscle tension can be painful, lead to bad posture, and create unpleasant daily experiences for many people. This is particularly true for people that hold unwanted tension in their iliacus and/or psoas muscles. Indeed, these muscles help form hip flexor muscles that aid in tilting of the pelvis and flexing of the thigh at the hip joint. They are also key in helping a person maintain proper body posture. However, engaging and relieving unwanted tension in the iliacus or psoas muscles is difficult because the muscles are positioned in the rear part of the lower abdomen, and various bones and other parts of the human body make direct access to those muscles difficult. Thus, there is a need for a muscle tension relief device that can easily and effectively access and relieve tension in the iliacus and psoas muscles.

BRIEF SUMMARY

Embodiments of the present invention provide a muscle tension relief device that can be utilized by an individual to relieve muscle tension. In this regard, some such example muscle tension relief devices can be used without the need for a physical therapist, even to engage hard to reach muscles, such as the iliacus and psoas muscles (e.g., the psoas major and minor muscles). Further, some such devices have a small size, and can be stored easily. This is particularly useful for home or gym usage.

Example muscle tension relief devices are also easy to use, which enables self-usage, although it can be useful with a physical therapist, such as for in-person or virtual visits. The shape and features of example muscle tension relief devices are designed to enable an individual to access either the iliacus muscle or the psoas muscles to offer tension relief. By laying on the device the muscle engagement feature (e.g., tip) can engage with and relieve tension in the user's muscles. Further, by merely shifting their weight, a user can cause the device to transition to a second position, resting on a different base portion. At the same time, the muscle engagement feature "turns" a corner within the user's lower abdomen (e.g., the user's lower quadrant) and engages the appropriate muscle (e.g., changing orientation to apply pressure at the proper position in, for example, the user's psoas major muscle). By providing distinct base portions along with starting and stopping positions, example devices provide stability and help ensure efficient and safe usage.

Some example muscle tension relief devices offer additional benefits such as being versatile so as to enable engagement of either the iliacus or psoas muscle—merely by changing orientation of the device. Further, the body of some of the muscle tension relief devices is shaped like the hand of a physical therapist—which helps the device engage the difficult to reach muscles, and provides the user with similar care and relief that they would otherwise only receive at the hands of a physical therapist.

In an example embodiment, an apparatus for relieving muscle tension is provided. The apparatus comprises a first base portion and a second base portion. The first base portion comprises a flat surface extending in a first plane and the second base portion comprises a flat surface extending in a second plane. A non-zero angle extends between the first plane and the second plane. The apparatus further includes a muscle engagement feature extending generally upwardly relative to the first base portion.

In some embodiments, the apparatus is configured to transition between a first position and a second position. When in the first position, the first base portion supports the apparatus on a surface with the second base portion lifted off the surface. When in the second position, the second base portion supports the apparatus on the surface with the first base portion lifted off the surface. In some embodiments, the apparatus is configured to transition from the first position to the second position based on a shift of weight of a user laying on the apparatus. In some embodiments, when the muscle engagement feature is engaged with a lower abdomen of the user, while the apparatus transitions from the first position to the second position, the muscle engagement feature changes orientation to apply pressure on one of an iliacus muscle or a psoas muscle of the user.

In some embodiments, the apparatus defines a front and a back. The first base portion defines a front edge and a back edge. The second base portion defines a front edge and a back edge. The back edge of the first base portion defines the back of the apparatus and the front edge of the second base portion defines the front of the apparatus. The muscle engagement feature further extends in a direction toward the front of the apparatus. In some embodiments, the apparatus is configured to transition from a first position to a second position based on a shift of weight of a user laying on the apparatus. When the apparatus is positioned beneath a lower abdomen of the user and oriented with the front of the apparatus toward a centerline of the user and with the muscle engagement feature engaged with the lower abdomen, while the apparatus transitions from the first position to the second position, the muscle engagement feature changes orientation to apply pressure on a psoas muscle of the user. In some embodiments, when the apparatus is positioned beneath the lower abdomen of the user and oriented with the front of the apparatus away from the centerline of the user and with the muscle engagement feature engaged with the lower abdomen, the muscle engagement feature engages an iliacus muscle of the user.

In some embodiments, the non-zero angle is between 1 degree and 30 degrees.

In some embodiments, the apparatus further comprises a body extending from the first base portion and the second base portion to the muscle engagement feature. In some embodiments, a portion of the body proximate the muscle engagement feature defines a shape and size corresponding to a portion of a human hand comprising at least three fingers positioned adjacently to each other. In some embodiments, the portion of the body proximate the muscle engagement feature defines a width that is less than a width of the first base portion. In some embodiments, the body defines an integral structure along with the first base portion and the second base portion. In some embodiments, the body comprises a first material, the muscle engagement feature comprises a second material, and the first material is different than the second material. In some embodiments, the second material is rubber. In some embodiments, the body defines a hole extending from a first side of the apparatus to a second side of the apparatus, and the hole is configured to receive a structure therethrough for hanging the apparatus.

In another example embodiment, an apparatus for relieving muscle tension is provided. The apparatus defines a front and a back. The apparatus comprises a first base portion defining a front edge and a back edge; and a second base portion defining a front edge and a back edge. The back edge of the second base portion is adjacent the front edge of the first base portion. The second base portion extends upwardly from the first base portion and toward the front of the apparatus. The apparatus further includes a muscle engagement feature extending in a direction generally upwardly relative to the first base portion and toward the front of the apparatus.

In some embodiments, the apparatus is configured to transition between a first position and a second position. When in the first position, the first base portion supports the apparatus on a surface with the second base portion lifted off the surface. When in the second position, the second base portion supports the apparatus on the surface with the first base portion lifted off the surface. In some embodiments, the apparatus is configured to transition from the first position to the second position based on a shift of weight of a user laying on the apparatus. When the apparatus is positioned beneath a lower abdomen of the user and oriented with the front of the apparatus toward a centerline of the user and with the muscle engagement feature engaged with the lower abdomen, while the apparatus transitions from the first position to the second position, the muscle engagement feature changes orientation to apply pressure on a psoas muscle of the user. In some embodiments, when the apparatus is positioned beneath the lower abdomen of the user and oriented with the front of the apparatus away from the centerline of the user and with the muscle engagement feature engaged with the lower abdomen, the muscle engagement feature engages an iliacus muscle of the user.

In yet another example embodiment an apparatus for relieving muscle tension is provided. The apparatus defines a front and a back. The apparatus comprises a first base portion and a second base portion. The second base portion extends in a direction upwardly relative to the first base portion and toward the front of the apparatus. The apparatus further includes a muscle engagement feature extending in a direction generally upwardly relative to the first base portion and toward the front of the apparatus. The apparatus further includes a body extending from the first base portion and the second base portion to the muscle engagement feature. A portion of the body proximate the muscle engagement feature defines a shape and size corresponding to a portion of a human hand comprising at least three fingers positioned adjacently to each other.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 14:
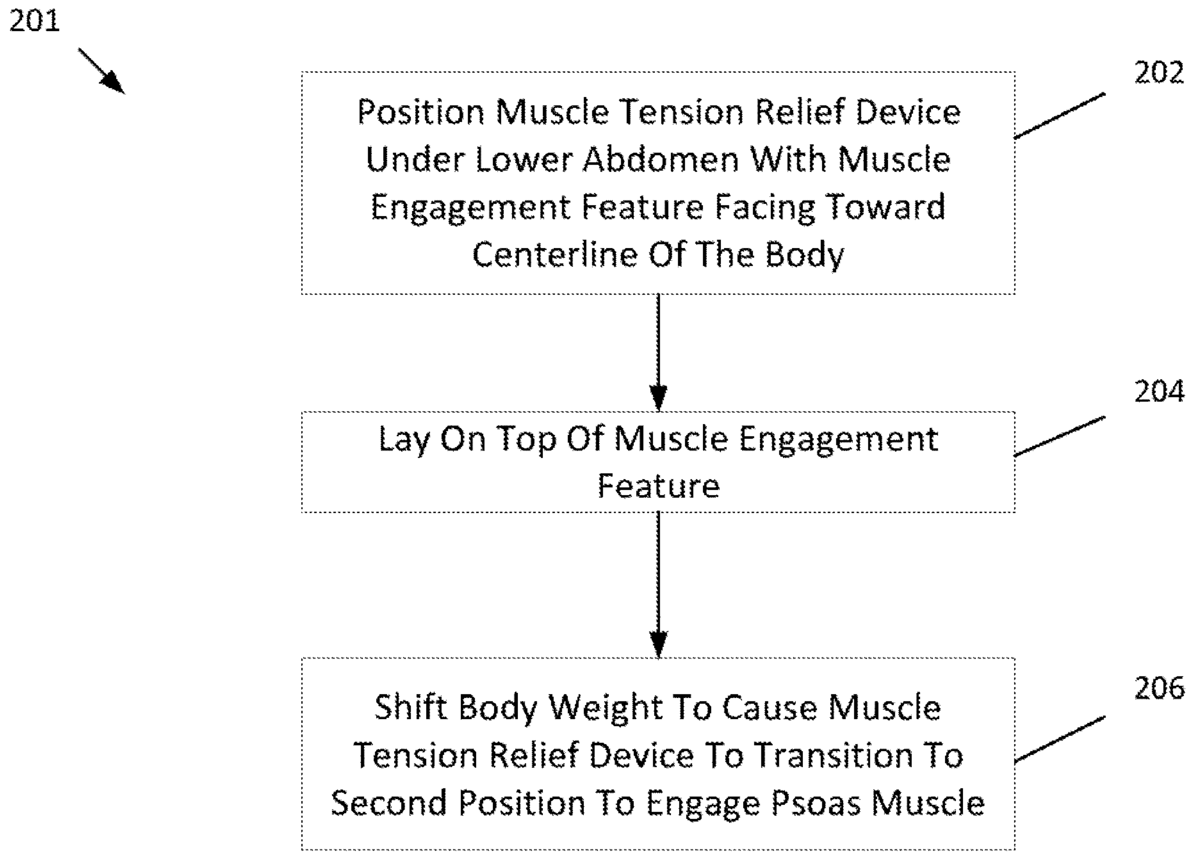
Figure 15:
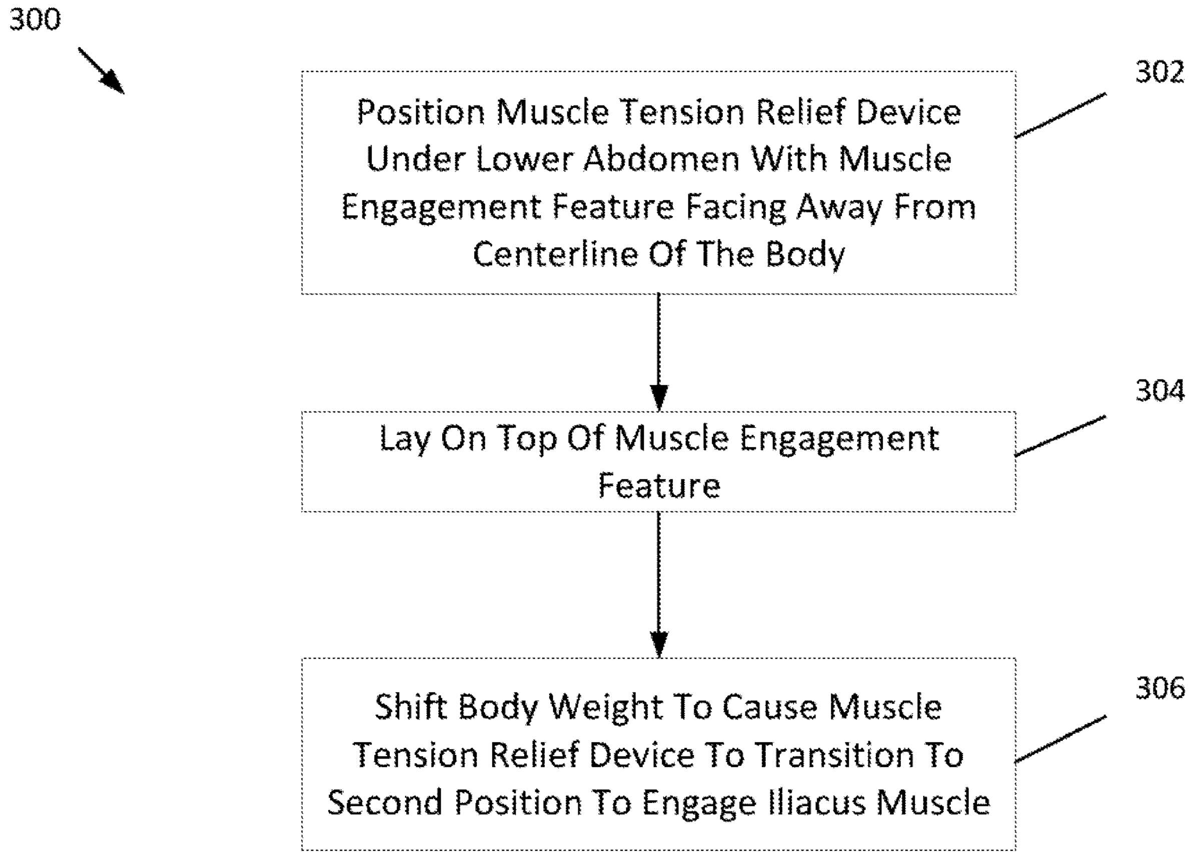

FIG. 14 illustrates a flowchart of an example method of utilizing the muscle tension relief device to engage and relieve tension in a user's psoas muscle, in accordance with some embodiments discussed herein; and FIG. 15 illustrates a flowchart of an example method of utilizing the muscle tension relief device to engage and relieve tension in a user's iliacus muscle, in accordance with some embodiments discussed herein.

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

Embodiments of the present invention provide a muscle tension relief device that can be utilized by an individual to relieve muscle tension. FIGS. 1-6 illustrate various views of an example muscle tension relief device 10. Though the following description focuses on the example muscle tension relief device 10, example embodiments of the present invention are not meant to be limited to the specifically shown device, as other types of devices that utilize various features and provide various benefits described herein are contemplated. For example, another example muscle tension relief device is shown and described with respect to FIG. 13. Further, use of the term "device" is not meant to be limiting, and various example embodiments may refer to the device as an apparatus, a tool, a massager, a tension reliever, among other things.

Figure 1:
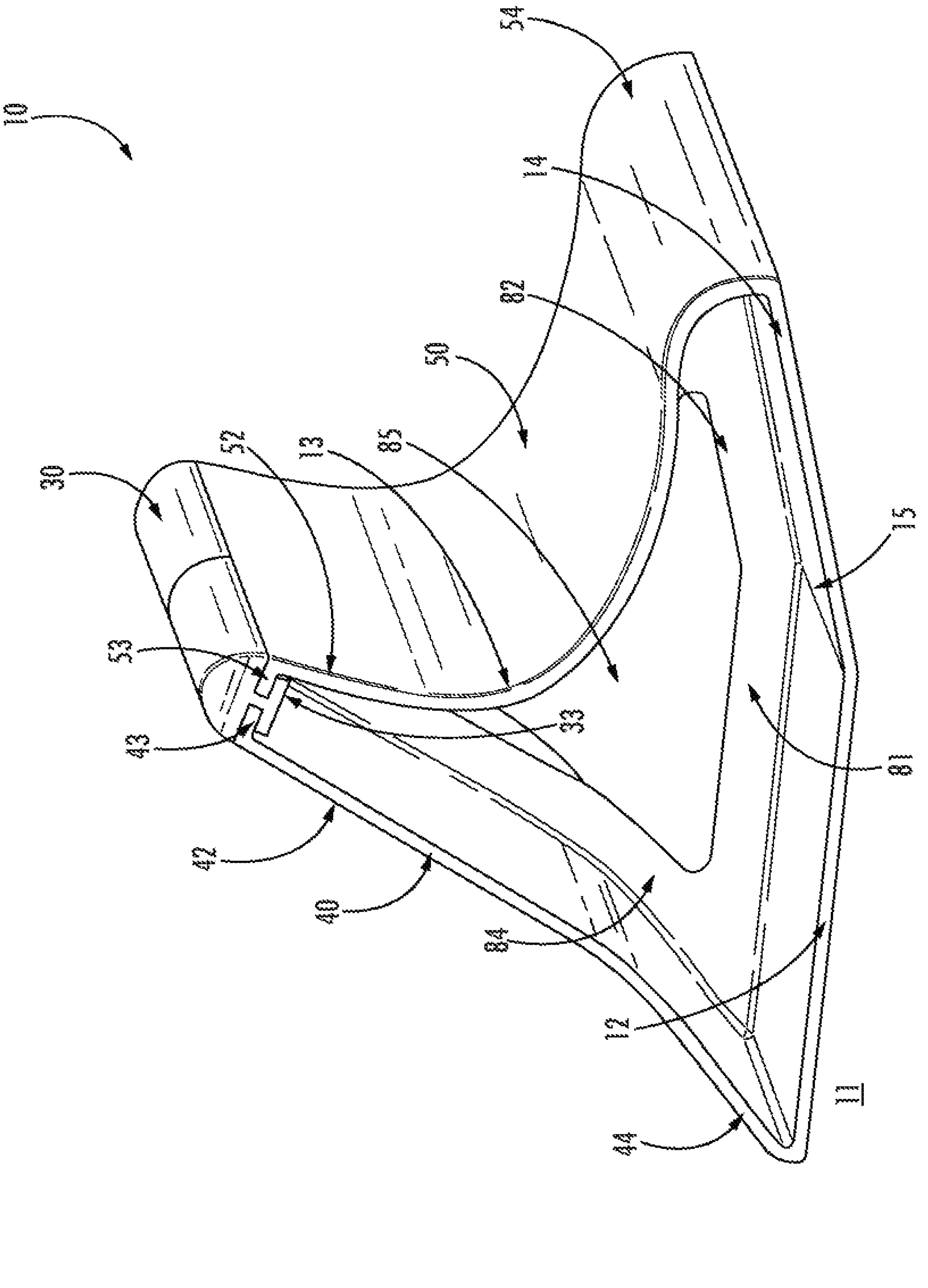
FIG. 1 shows a perspective view of a muscle tension relief device, in accordance with some embodiments discussed herein.

FIG. 1 shows an example muscle tension relief device 10. The muscle tension relief device 10 includes a body 13 and a muscle engagement feature 30. Notably, while shown as separate pieces, in some embodiments, the muscle engagement feature 30 may be integral with the body 13

Notably, in some embodiments, the relative size of the muscle tension relief device 10 is designed to be relatively small so as to maintain a small footprint for ease of use, carrying, and storage. For example, the muscle tension relieve device 10 may define an overall length of 8-10 in. front to back, overall width of 3-6 in. side to side, and overall height of 4-10 in.

The body 13, in the illustrated embodiment, forms an integrally-molded single piece. However, in other embodiments, the body 13 may be formed of multiple pieces. The body 13 comprises a front wall 50, a back wall 40, a first base portion 12, and a second base portion 14. The body 13 also includes, in the illustrated embodiment, complimentary body attachment features 43, 54 that are spaced apart to enable a "T" slot connection feature 33 of the muscle engagement feature 30 to be secured therein.

Figure 2:
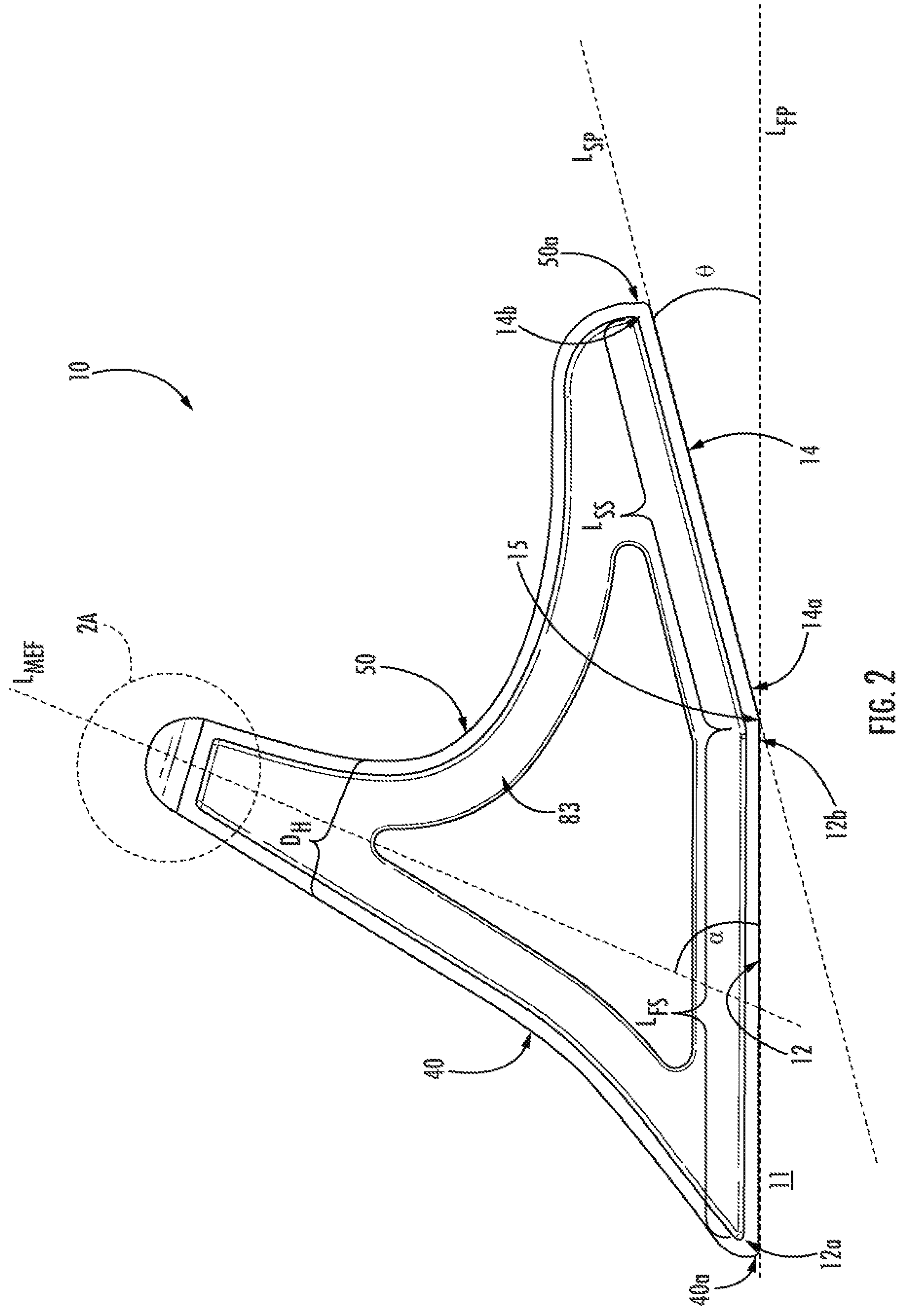
FIG. 2 shows a side view of the example muscle tension relief device shown in FIG. 1, in accordance with some embodiments discussed herein.
Figure 4:
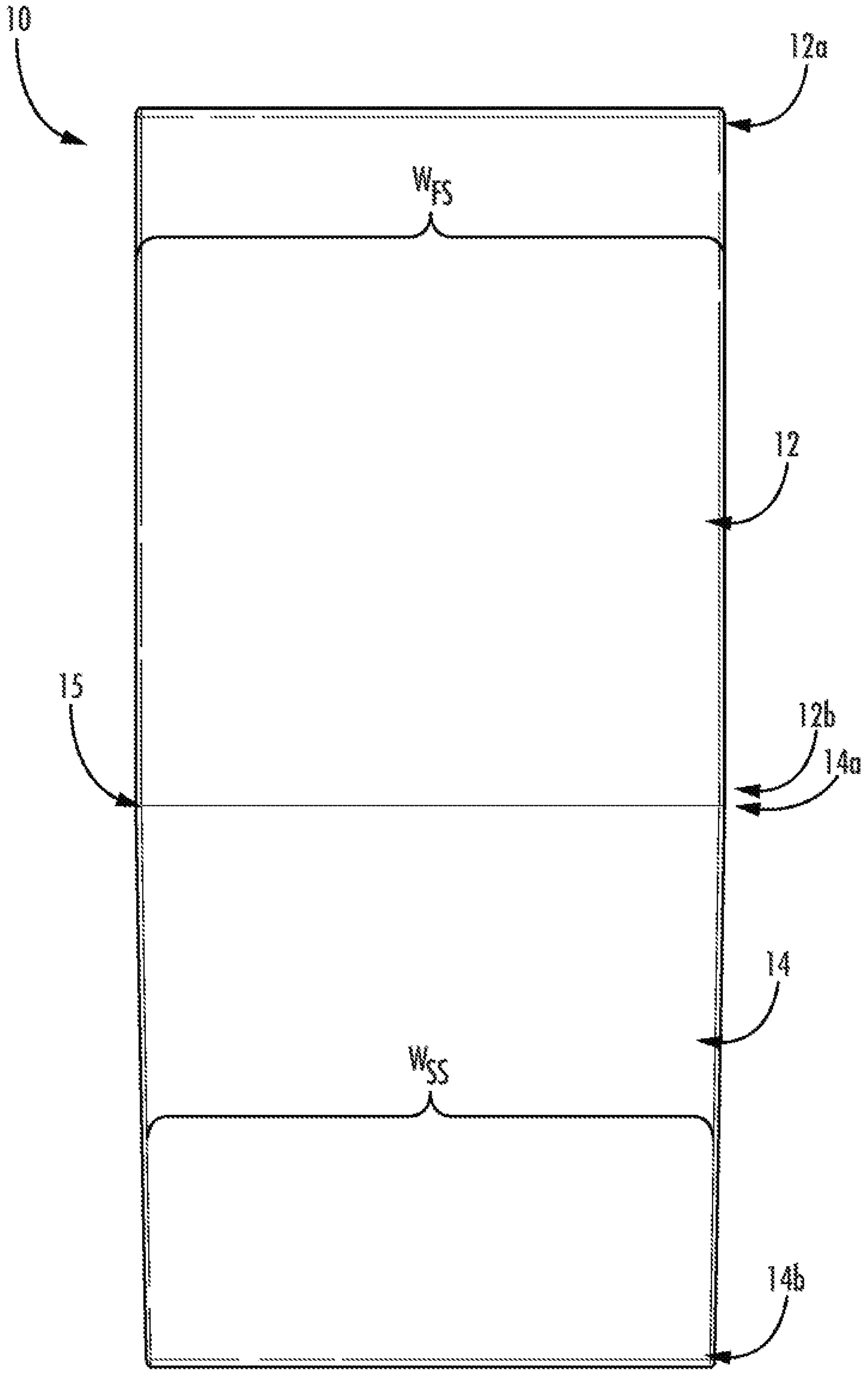
FIG. 4 shows a bottom view of the example muscle tension relief device shown in FIG. 1, in accordance with some embodiments discussed herein.

With reference to FIGS. 1 and 2, the first base portion 12 defines a flat surface extending from a back edge 12*a* to a front edge 12*b*. The back edge 12*a* is adjacent a bottom edge 40*a* of the back wall 40. The front edge 12*b* is adjacent a back edge 14*a* of the second base portion 14. With reference to FIGS. 2 and 4, the first base portion 12 defines a length $L_{FS}$ and width $W_{FS}$. In some example embodiments, the length $L_{FS}$ of the first base portion 12 may be ~4.75 in., and the width $W_{FS}$ may be ~4 in. As illustrated in FIGS. 1 and 2, the muscle tension relief device 10 is configured to rest on the ground 11 via the first base portion 12 when in the first position. In some embodiments, the first base portion 12 may include a non-slip grip, such as an attached one or more portions of non-slip grip or being integrally-formed with features that provide the benefits of a non-slip grip (e.g., ridges, stippling, etc.). In this regard, the first base portion 12, which may rest on the ground, is configured to prevent slippage of the muscle tension relief device 10—such as while a user is laying on the muscle tension relief device 10 as described herein.

Figure 6:
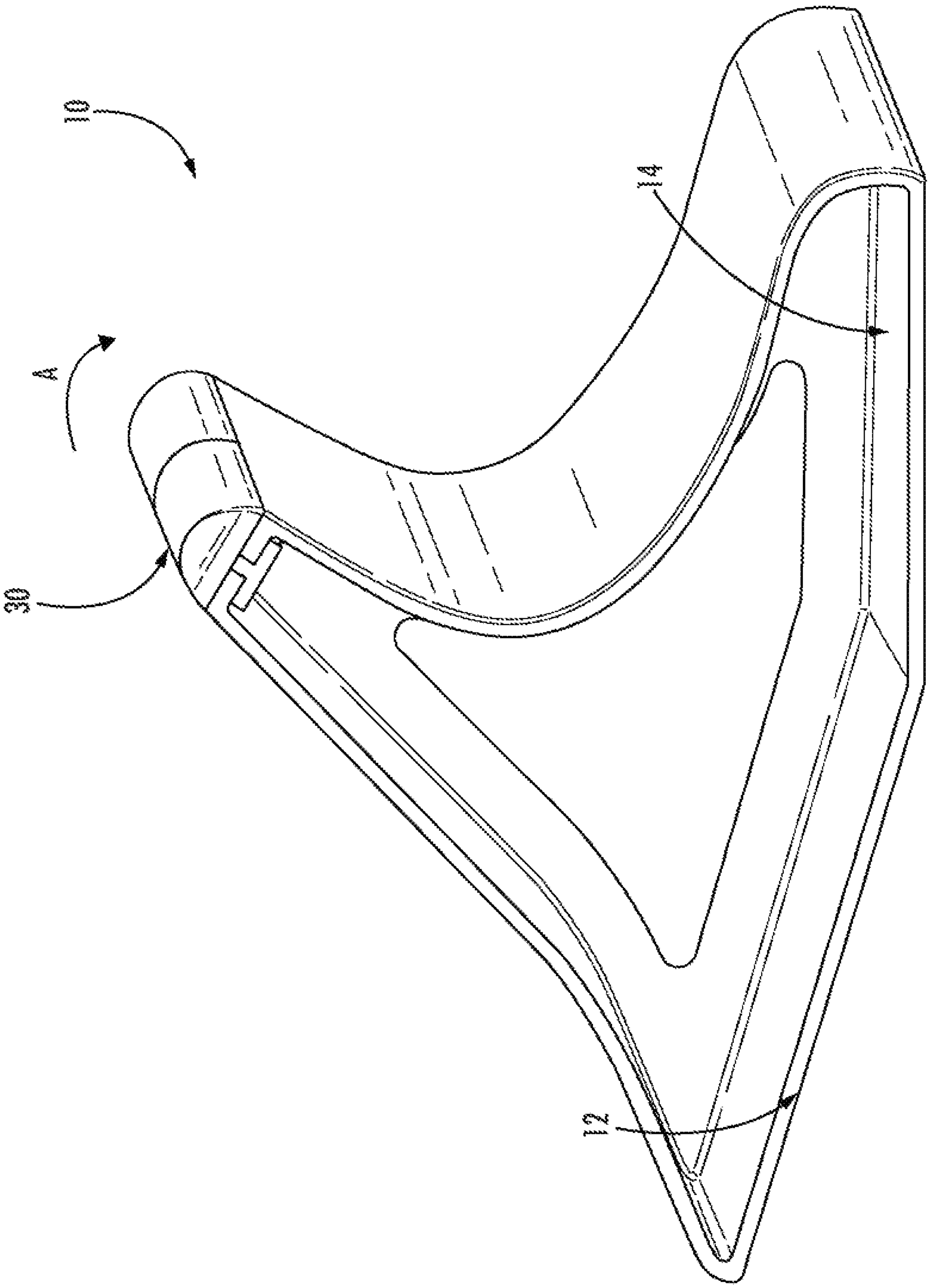
FIG. 6 shows the example muscle tension relief device shown in FIG. 1, wherein the muscle tension relief device has rotated to a second position, in accordance with some embodiments discussed herein.

With reference to FIGS. 1 and 2, the second base portion 14 defines a flat surface extending from a back edge 14*a* to a front edge 14*b*. The back edge 14*a* is adjacent a front edge 12*a* of the first base portion 12. The front edge 12*b* is adjacent a bottom edge 50*a* of the front wall 50. With reference to FIGS. 2 and 4, the second base portion 14 defines a length $L_{SS}$ and width $W_{SS}$. In some example embodiments, the length $L_{SS}$ of the second base portion 14 may be ~4 in., and the width $W_{SS}$ may be ~4 in. As illustrated in FIG. 6, the muscle tension relief device 10 is configured to rest on the ground 11 via the second base portion 14 when in the second position. In some embodiments, the second base portion 14 may include a non-slip grip, such as an attached one or more portions of non-slip grip or being integrally-formed with features that provide the benefits of a non-slip grip (e.g., ridges, stippling, etc.). In this regard, the second base portion 14, which may rest on the ground, is configured to prevent slippage of the muscle tension relief device 10—such as while a user is laying on the muscle tension relief device 10 as described herein.

The front wall 50, in the illustrated embodiment, defines a concave shape extending from a front end 54 to a top end 52. At the front end 54, the front wall 50 further defines a convex shaped curve leading to the bottom edge 50*a*. An attachment feature 53 in the form of a lip extends from the front wall 50 near the top end 52.

The back wall 40, in the illustrated embodiment, defines a slight concave curve leading from a bottom edge 40*a* at bottom end 44 to a top end 42. An attachment feature 43 in the form of a lip extends from the back wall 40 near the top end 42.

The muscle engagement feature 30 is configured to extend from the muscle tension relief device 10 and engage with a muscle of the user to provide relief from tension in the muscle. In the illustrated embodiment, the muscle engagement feature 30 extends in a generally upward and forward direction (e.g., with respect to the first base portion 12 and toward the front of the muscle tension relief device 10). In some embodiments, the muscle engagement feature 30 is designed to be the uppermost surface of the muscle tension relief device 10 to ensure that it touches the user's body first during use. Further, in some embodiments, the muscle engagement feature 30 may extend in a plane $L_{MEF}$ that forms an angle (e.g., angle $\alpha$) with respect to the first base portion 12 to help ensure that a proper positioning of pressure is applied through the muscle tension relief device 10 into the user's muscle. In some embodiments, the angle $\alpha$ may range from 30° to 80°, with a preferred range of 60° to 80°. Such an angle $\alpha$ may also be used in conjunction with the ability of the muscle tension relief device 10 to transition from a first position (FIG. 1) to a second position (FIG. 6) to help the muscle engagement feature 30 access, engage with, and provide relief for certain muscles (such as the psoas major muscle).

In some embodiments, the muscle engagement feature 30 (or a portion thereof) may be formed of a different material than the body 13 of the muscle tension relief device 10. For example, the muscle engagement feature 30 may be formed of rubber or similar material, providing some cushion and pliable surface for engagement with a user. In contrast, the body 13 may be formed of plastic material or other more rigid structure. Alternatively, the muscle engagement feature 30 may be formed of the same material as the body 13 or other parts of the muscle tension relief device 10.

In some embodiments, the muscle engagement feature 30 may form a separate structure than the body 13 such that the muscle engagement feature 30 may be attached to the body 13. For example, with reference to FIG. 1, the muscle engagement feature 30 may include a connection feature 33 that is configured to enable attachment/connection of the muscle engagement feature 30 to the body 13. For example, the connection feature 33 may form a "T" shape with a center portion 33*a* that can fit between the attachment features 43, 53 of the body 13. A flat end portion 33*b* of the connection feature 33 may rest on a side of the attachment features 43, 53 opposite the remainder of the muscle engagement feature 30 to ensure connection of the muscle engagement feature 30 to the body 13. Notably, other connection means to attach/connect the muscle engagement feature 30 to the body 13 are also contemplated (e.g., interference fit, adhesive, fasteners, etc.).

Figure 2A:
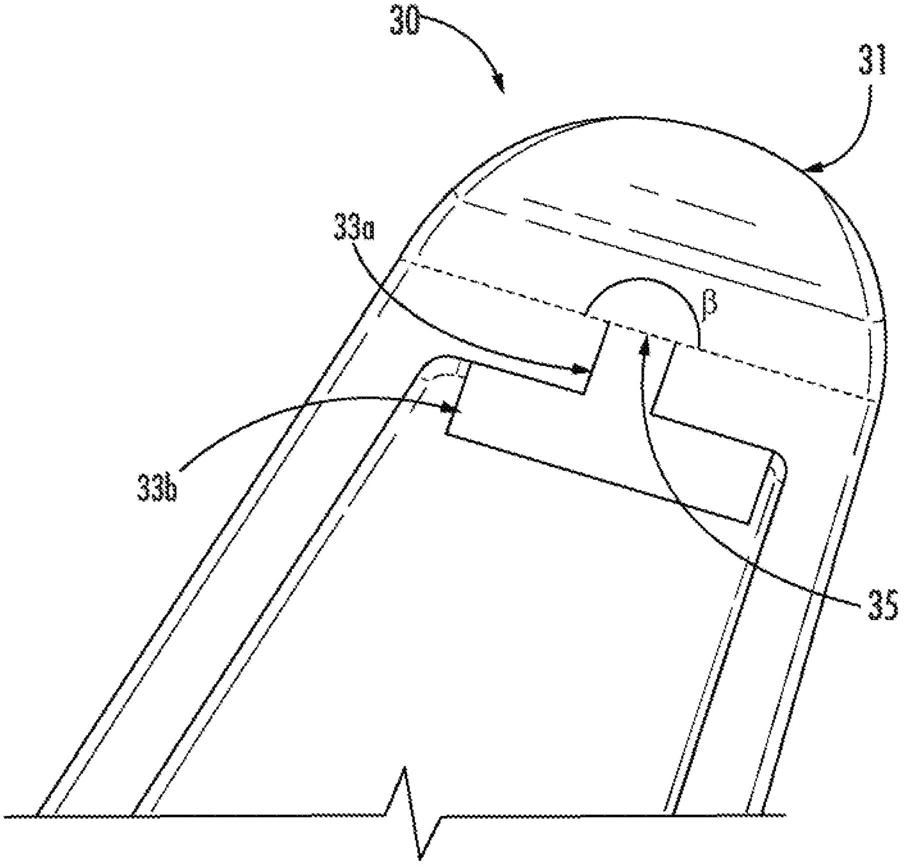
FIG. 2A illustrates a close-up view of a portion of the muscle tension relief device indicated as 2A in FIG. 1, in accordance with some embodiments discussed herein.

In some embodiments, the muscle tension relief device 10 may be configured to mimic a hand, such as a hand of a physical therapist. This helps provide the user of the muscle tension relief device 10 the benefits achieved by a physical therapist, without actually needing another person. For example, with reference to FIG. 2A, the muscle engagement feature 30 may include a curvature that mimics the fingertips of a hand. For example, the outer surface 31 of the muscle engagement feature 30 may define a curvature β with respect to a center axis 35 that is similar to that of a tip portion of a finger.

Figure 3:
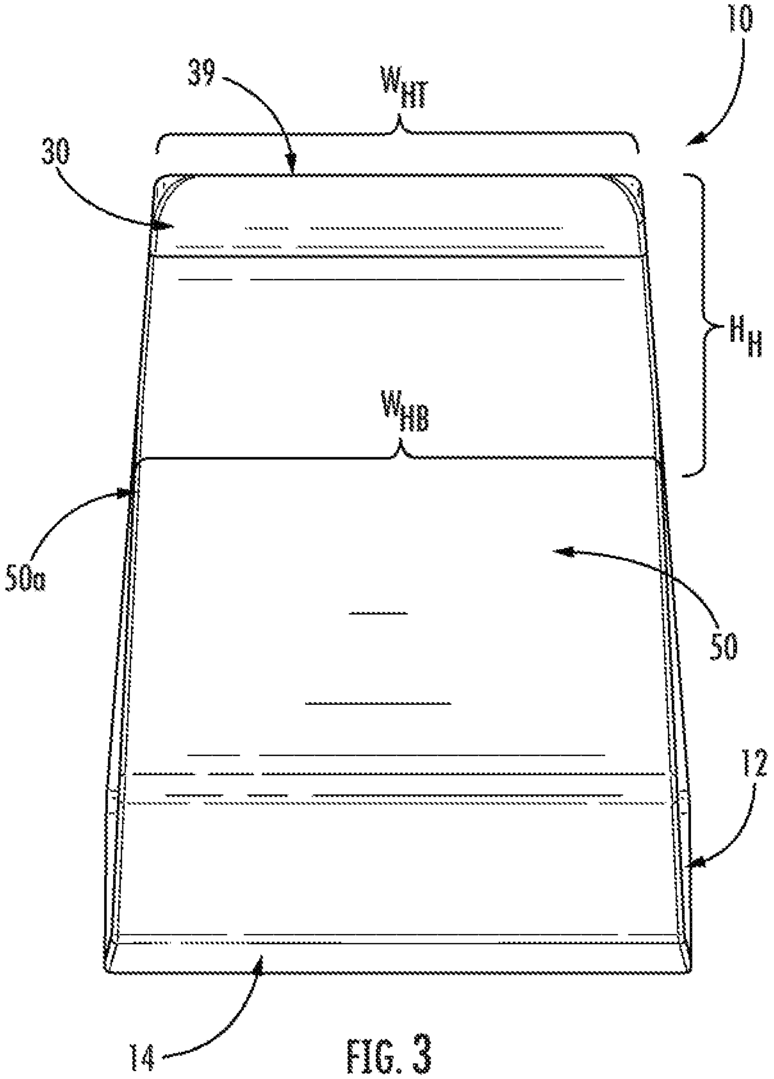
FIG. 3 shows a front view of the example muscle tension relief device shown in FIG. 1, in accordance with some embodiments discussed herein.

Along these lines, with reference to FIG. 3, the muscle engagement feature 30 and an upper portion of the body 13 proximate the muscle engagement feature 30 may define a shape and/or size the corresponds to a human hand (or a portion thereof). With reference to FIG. 3, the portion of the body 13 and the muscle engagement feature 30 being referred to include the general shape outlined by the width at the top of the muscle engagement feature $W_{HT}$, the width at a generally center portion of the front wall 50 and back wall 40—defined as width $W_{HB}$, the height $H_H$ from the center portion of the front wall 50 and back wall 40 to the top of the muscle engagement feature 30, and the depth $D_H$ from the front wall 50 to the back wall 40 (shown in FIG. 2). While the various measurements indicated above can vary, the goal size and shape correspond to a hand, such as with at least three adjacently positioned fingers being represented, although the design illustrated corresponds to four fingers being represented. Some example measurements include a width at the top of the muscle engagement feature $W_{HT}$ between 1 in.-3 in.; a width at a generally center portion of the front wall 50 and back wall 40 defined as width $W_{HB}$ between 1 in.-4 in.; the height $H_H$ from the center portion of the front wall 50 and back wall 40 to the top of the muscle engagement feature 30 between 1 in.-4 in., and the depth $D_H$ from the front wall 50 to the back wall 40 between 0.25 in.-1.5 in. Further, as noted above, in some embodiments, the curvature of the muscle engagement feature 30 may correspond to the curvature of fingertips of a human hand. Of this working together to create a portion of the muscle tension relief device 10 that is designed to mimic the effects of a human hand during usage of the muscle tension relief device 10.

Figure 5:
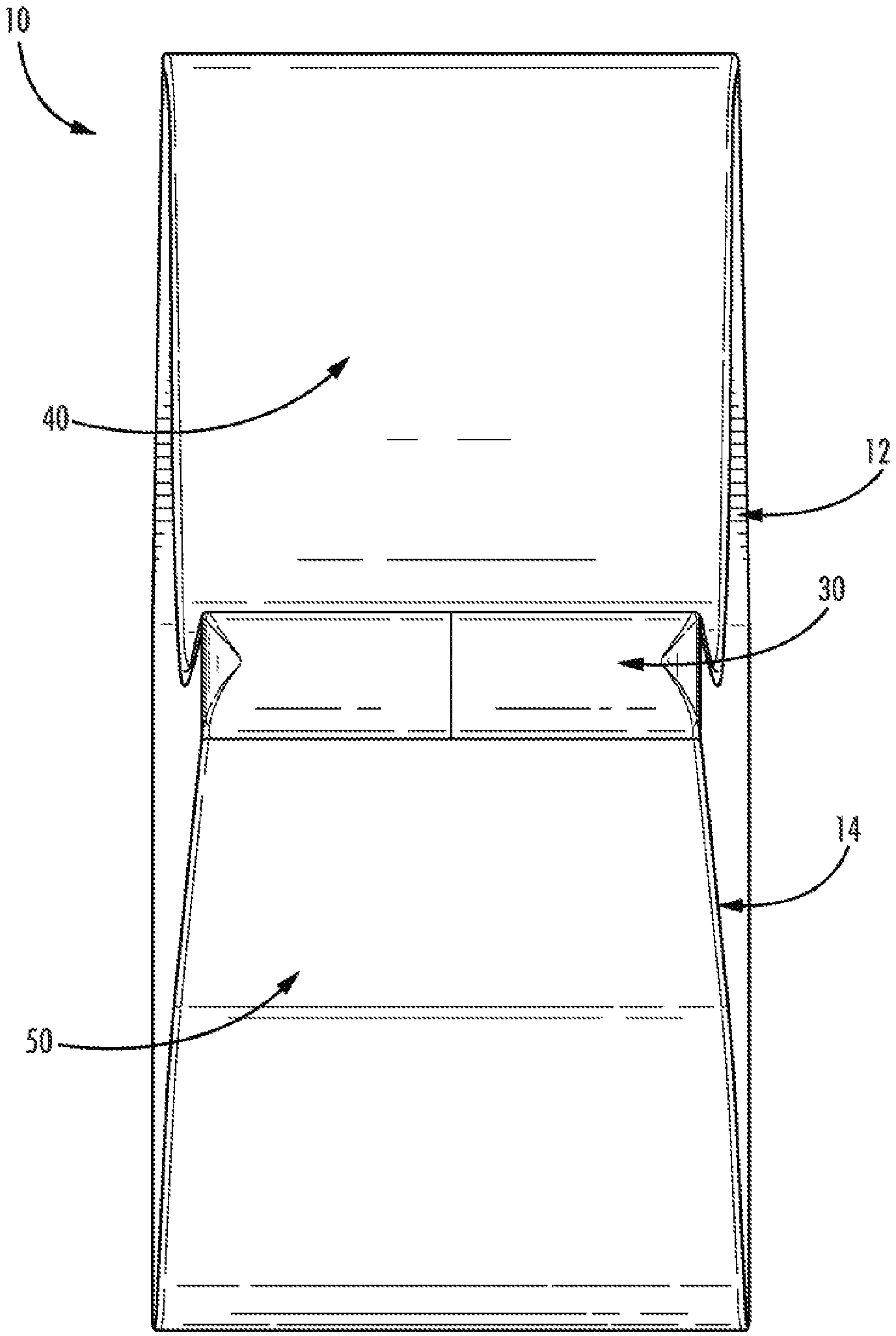
FIG. 5 shows a top view of the example muscle tension relief device shown in FIG. 1, in accordance with some embodiments discussed herein.

As indicated herein, in some embodiments, the muscle tension relief device 10 is designed to rest on one of the first base portion 12 or the second base portion 14. Notably, the muscle tension relief device 10 is also designed to safely withstand the weight of an individual being pressed thereon. In this regard, the first base portion 12 and the second base portion 14 define a size and shape that achieve that safety. In some embodiments, however, the desired shape of the upper portion of the body 13 and the muscle engagement feature 30 (e.g., corresponding to a hand shape) may be less than the desired shape and size of each base portion (e.g., the width at the top of the muscle engagement feature $W_{HT}$ may be less than the width $W_{FS}$ of the first base portion 12). Thus, in some embodiments, the body 13 defines a taper leading from the base portions upwardly toward the muscle engagement feature 30. This is best illustrated in FIG. 5.

Returning to FIG. 1, in some embodiments, the muscle tension relief device 10 may include one or more reinforcement ribs that help provide stability, which may (depending on the design) be important since a user will lay on the muscle tension relief device 10. In the illustrated embodiment, the muscle tension device includes a front wall rib 83 for reinforcing the front wall 50 (shown in FIG. 2), a back wall rib 84 for reinforcing the back wall 40, a first base rib 81 for reinforcing the first base portion 12, and a second base rib 82 for reinforcing the second base portion 14. In some embodiments, more or less ribs are contemplated and/or other reinforcing features are contemplated (e.g., double walls, multiple spaced apart ribs, etc.).

As indicated herein, in some embodiments, the muscle tension relief device 10 is configured to transition between at least a first position and a second position. The ability to transition between positions enables the orientation of the muscle engagement feature to change to apply pressure at proper points in a user's muscle. As detailed herein, the illustrated muscle tension device 10 is specifically designed to enable proper pressure to be provided to the iliacus and psoas muscles.

FIGS. 1 and 2 illustrate the muscle tension relief device 10 in the first position, with the first base portion 12 resting on the ground 11 (although other surfaces are contemplated). The first base portion 12 defines a flat surface that extends in a first base plane LFP. The second base portion 14, which extends forwardly and upwardly from the first base portion 12, defines a flat surface that extends in a second base plane LSP. Notably, there is a non-zero angle θ defined between the first base plane LFP and the second base plane LSP. In some embodiments, the angle θ is between 1° and 30°, with a preferred range between 1° and 5°. In the illustrated embodiment, the angle θ is ~2°. Notably, by including a non-zero angle θ, the muscle tension relief device can transition (e.g., along arrow A in FIG. 6) between a first position resting on the first base portion 12 (shown in FIGS. 1 and 2) to a second position resting on the second base portion 14 (shown in FIG. 6). In the first position, the second base portion 14 is off the ground 11; and, in the second position, the first base portion 12 is off the ground 11.

With reference to FIG. 2, in some embodiments, the muscle engagement feature 30 may be positioned laterally relatively closer to the front edge 12*b* of the first base portion 12 than the back edge 12*a* of the first base portion 12. In such a configuration, when a user rests their weight on the muscle engagement feature 30, there is a natural bias (with a little weight shift) that is created to cause the muscle tension relief device 10 to transition to the second position.

As noted herein, one benefit of example muscle tension relief devices 10 with first and second base portions, is that they provide a safety stop during use of the muscle tension relief devices 10. For example, the hard stop of the muscle tension relief device 10 resting on the second base portion 14 prevents further rotation of the muscle tension relief device 10, which may otherwise cause discomfort to the user.

Although the illustrated embodiment is designed to achieve two positions, in some embodiments, additional positions may be achieved with addition base portions. For example, a middle base portion (extending at a slightly different lower angle) may form an intermediate position for the muscle tension relief device.

Figure 7:
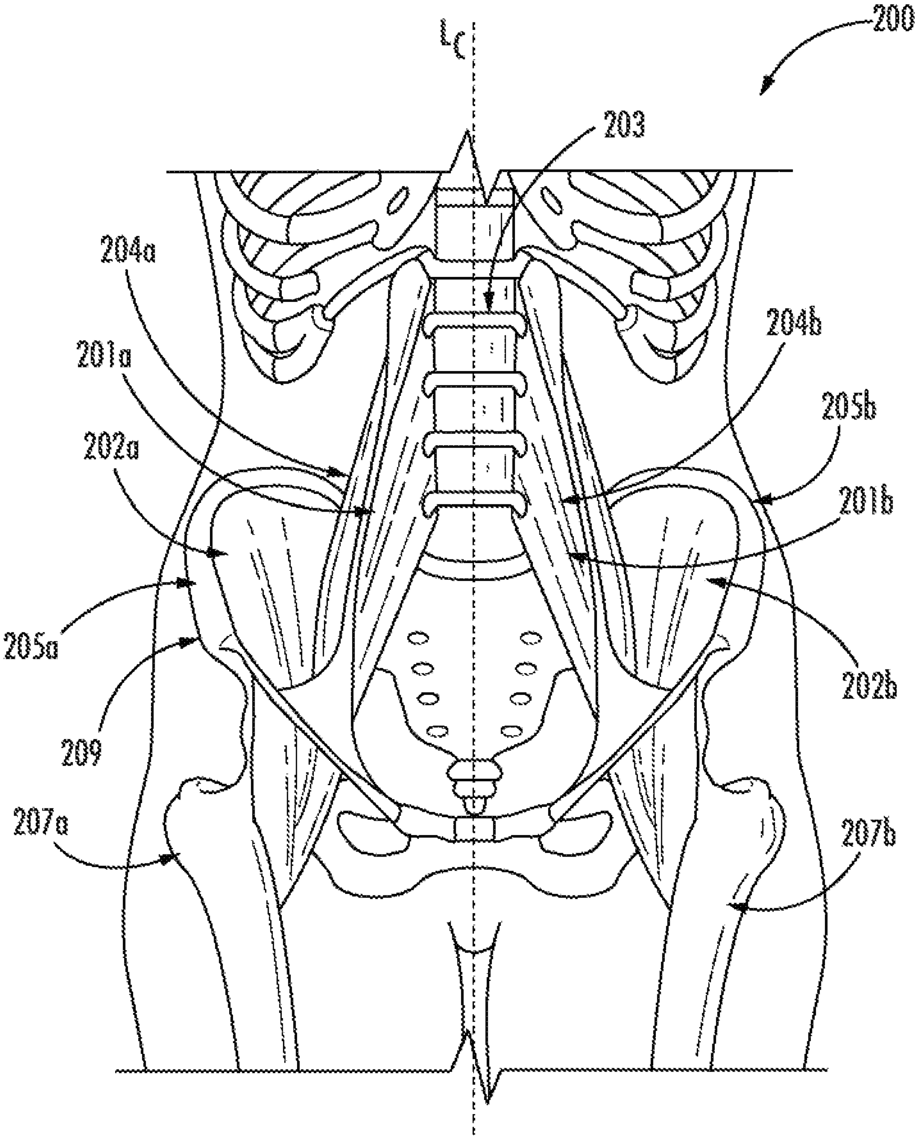
FIG. 7 illustrates a partially transparent view of a lower abdomen of a human body, wherein the iliacus and psoas muscles are shown, in accordance with some embodiments discussed herein.

FIG. 7 illustrates a partially transparent view of a lower abdomen portion of a human body. Notably, the illustration in FIG. 7 highlights the iliacus muscles 202*a*, 202*b* and psoas muscles 204*a*, 204*b* (including psoas major muscle 201*a*, 201*b*). Notably, the iliacus muscles 202*a*, 202*b* are each attached to the hip bone 205*a*, 205*b* at one end and the leg bone 207*a*, 207*b* at the other end. The psoas muscles 204*a*, 204*b* extend between the spine 203 (at the $12^{th}$ thoracic vertebrae and $5^{th}$ lumbar vertebrae), through the pelvis, and the femurs. A centerline $L_C$ of the body 200 illustrates that the iliacus and psoas muscles extend symmetrically on both sides of the body 200. As illustrated, the iliacus and psoas muscles are positioned in the rear part of the body 200 and, thus, are difficult to reach—making providing tension relief in those muscles difficult. However, embodiments of the present invention, provide a muscle tension relief device 10 designed specifically to target each of those particular muscles.

Figure 8:
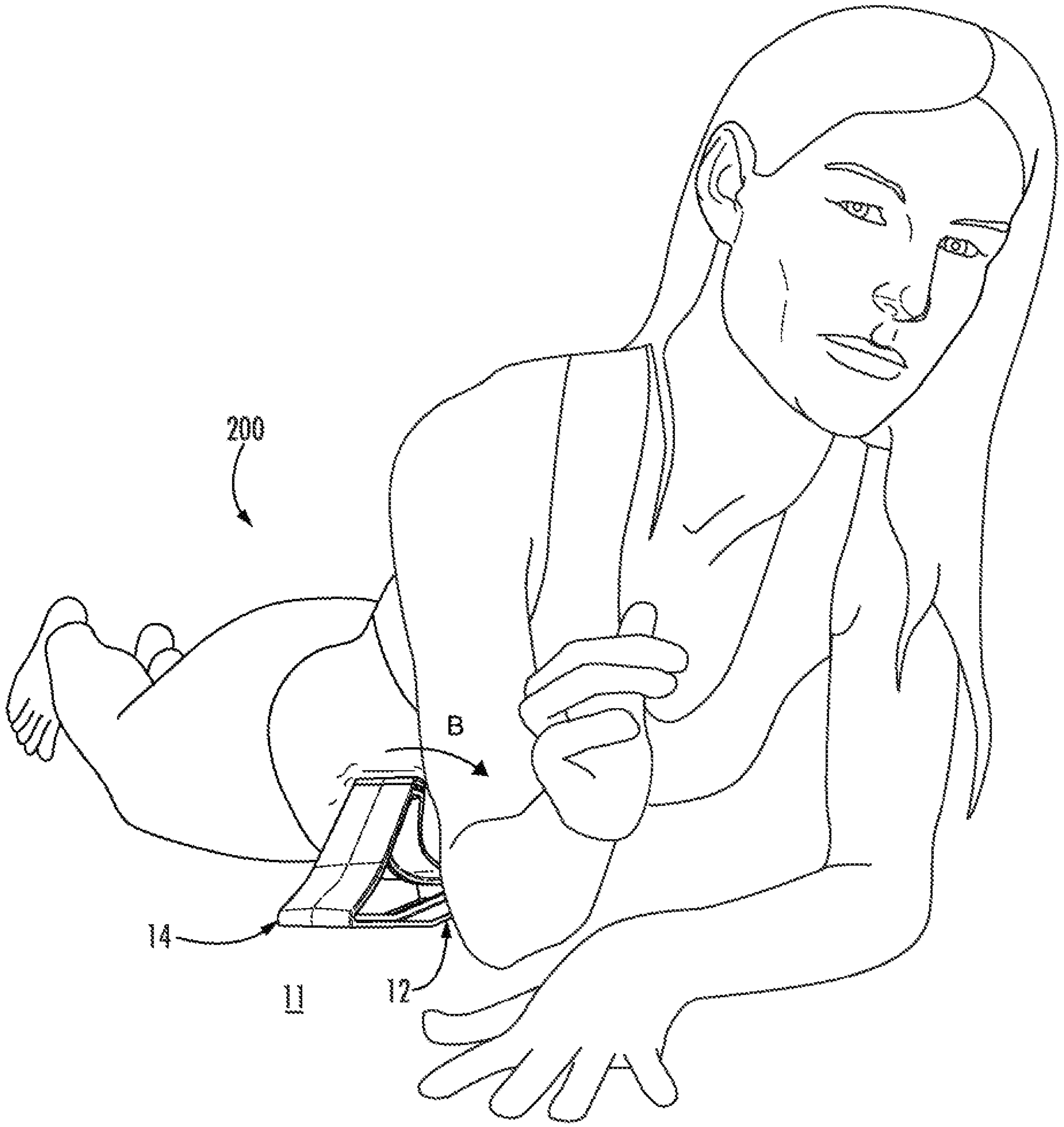
FIG. 8 illustrates a user interacting with the example muscle tension relief device shown in FIG. 1, wherein the muscle tension relief device is positioned in a first position to engage the psoas muscle of the user, in accordance with some embodiments discussed herein.
Figure 9:
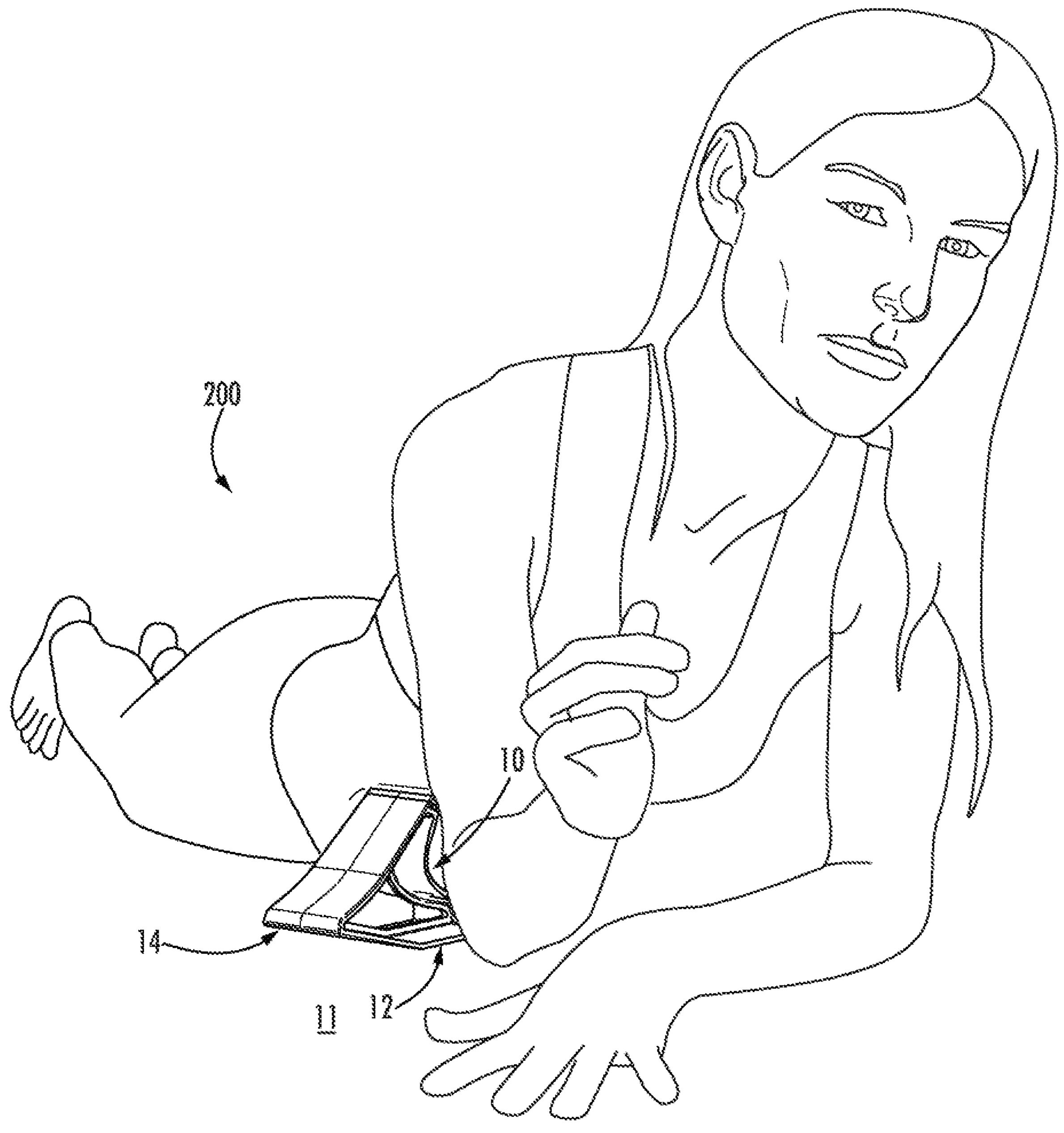
FIG. 9 illustrates that the user has shifted their weight to cause the example muscle tension relief device to rotate to a second position where a muscle engagement feature of the muscle tension relief device has engaged the psoas muscle of the user, in accordance with some embodiments discussed herein.

FIGS. 8-9 illustrate a user interacting with the example muscle tension relief device 10 shown in FIG. 1 to provide relief to the psoas muscle. FIG. 14 illustrates a flowchart according to an example method 201 of such. As shown, a user 200 positions and lays on the muscle tension relief device 10 such that the muscle engagement feature 30 is engaged with their lower abdomen and pointing generally toward the user's psoas muscle (and toward the centerline of the user's body) with the longitudinal dimension of the muscle engagement feature 30 extending parallel to the user's body centerline (e.g., operations 202 and 204 shown in FIG. 14). In FIG. 8, the muscle tension relief device 10 is resting in a first position with the first base portion 12 on the ground 11. Upon shifting of the user's weight, the muscle tension relief device 10 transitions (e.g., along arrow B shown in FIG. 8) from the first position to a second position so as to rest with the second base portion 14 on the ground 11 (shown in FIG. 9) (e.g., operation 206 shown in FIG. 14). During that transition, the muscle engagement feature 30 changes orientation to navigate the internal parts of the user's body and engages the psoas muscle to apply pressure thereon and provide tension relief. The user can engage the other psoas muscle by rotating the muscle tension relief device 10 and moving it to the other side of their body.

Figure 10:
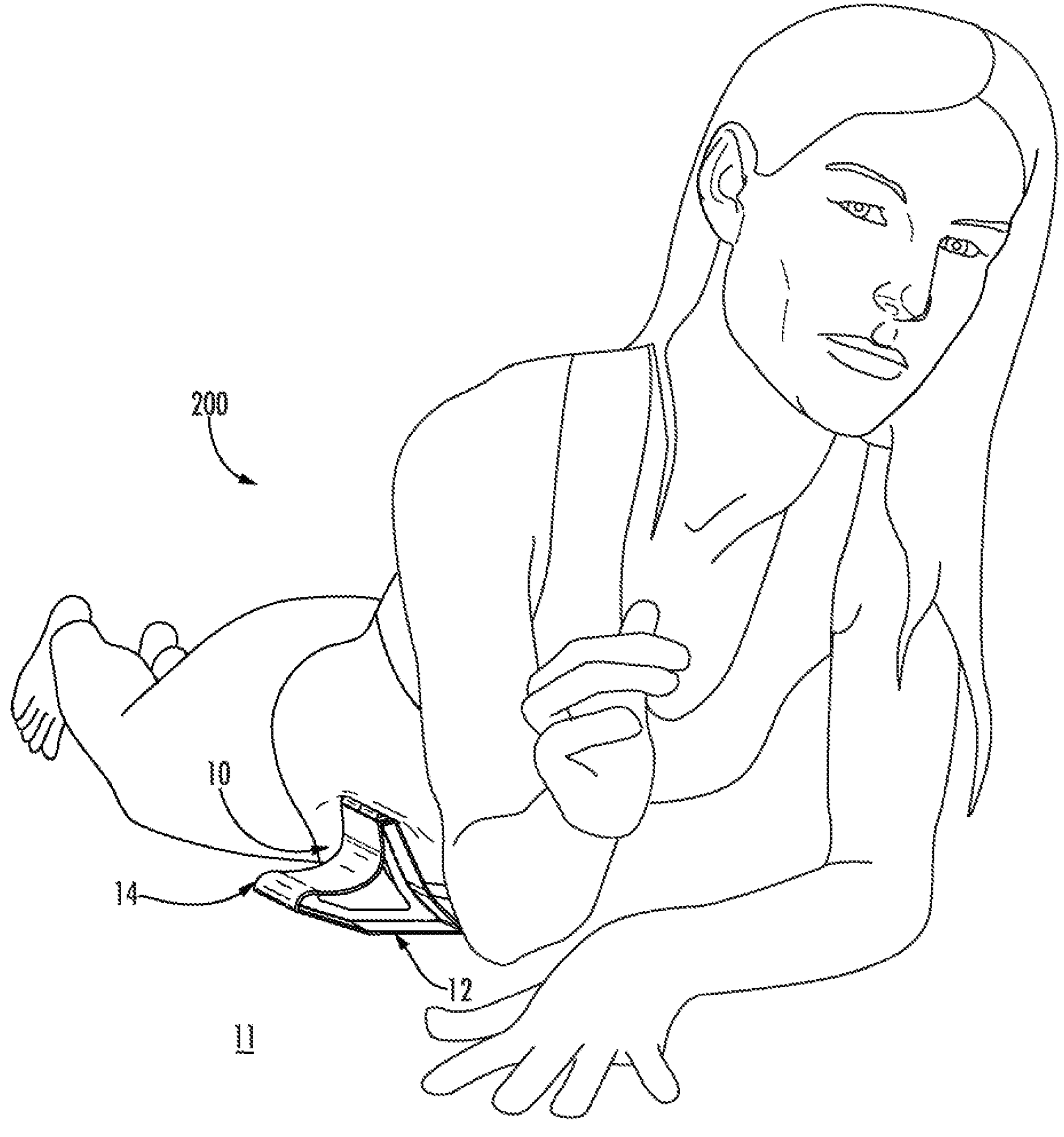
FIG. 10 illustrates a user interacting with the example muscle tension relief device shown in FIG. 1, wherein the muscle tension relief device is re-oriented from its facing direction shown in FIG. 8, and wherein the muscle tension relief device is positioned in a first position to engage the iliacus muscle of the user, in accordance with some embodiments discussed herein.
Figure 11:
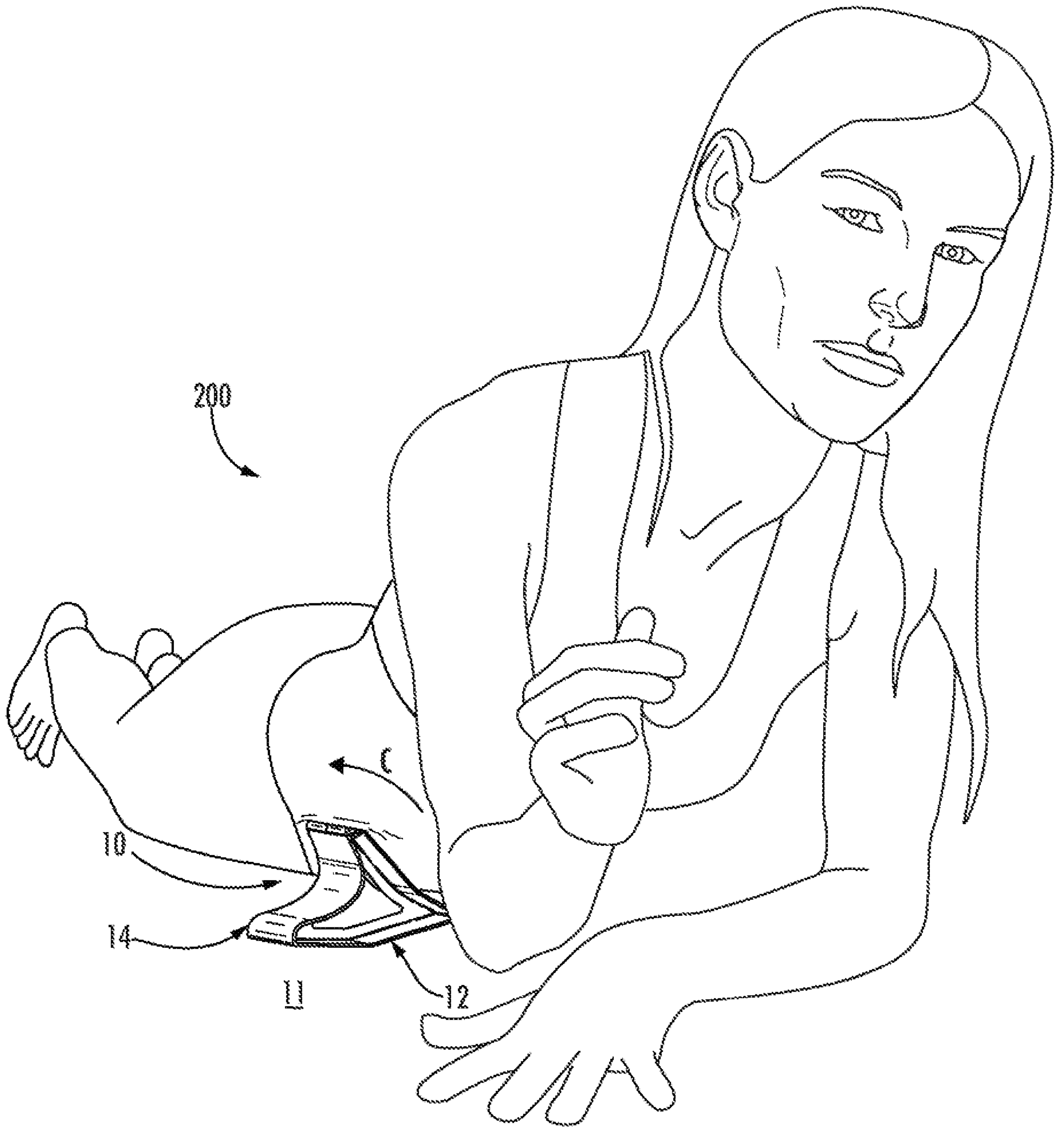
FIG. 11 illustrates that the user has shifted their weight to cause the example muscle tension relief device to rotate to a second position, in accordance with some embodiments discussed herein.

Notably, the muscle tension relief device 10 is useable to engage either the psoas muscle or the iliacus muscle. In this regard, the user merely needs to change the direction of the muscle tension relief device 10 and slight reposition it to engage the iliacus muscle. For example, FIGS. 10-11 illustrate a user interacting with the example muscle tension relief device 10 shown in FIG. 1 to provide relief to the iliacus muscle. FIG. 15 illustrates a flowchart according to an example method 300 of such. As shown, a user 200 positions and lays on the muscle tension relief device 10 such that the muscle engagement feature 30 is engaged with their lower abdomen and pointing generally toward the user's iliacus muscle (and away from the centerline of the user's body) with the longitudinal dimension of the muscle engagement feature 30 extending parallel to the user's body centerline (e.g., operations 302 and 304 shown in FIG. 15). In FIG. 10, the muscle tension relief device 10 is resting in a first position with the first base portion 12 on the ground 11. Upon shifting of the user's weight, the muscle tension relief device 10 transitions (e.g., along arrow B) from the first position to a second position so as to rest with the second base portion 14 on the ground 11 (shown in FIG. 11) (e.g., operation 306 shown in FIG. 15). During that transition, the muscle engagement feature 30 changes orientation to navigate the internal parts of the user's body and engages the iliacus muscle to apply pressure thereon and provide tension relief. The user can engage the other iliacus muscle by rotating the muscle tension relief device 10 and moving it to the other side of their body.

Figure 12:
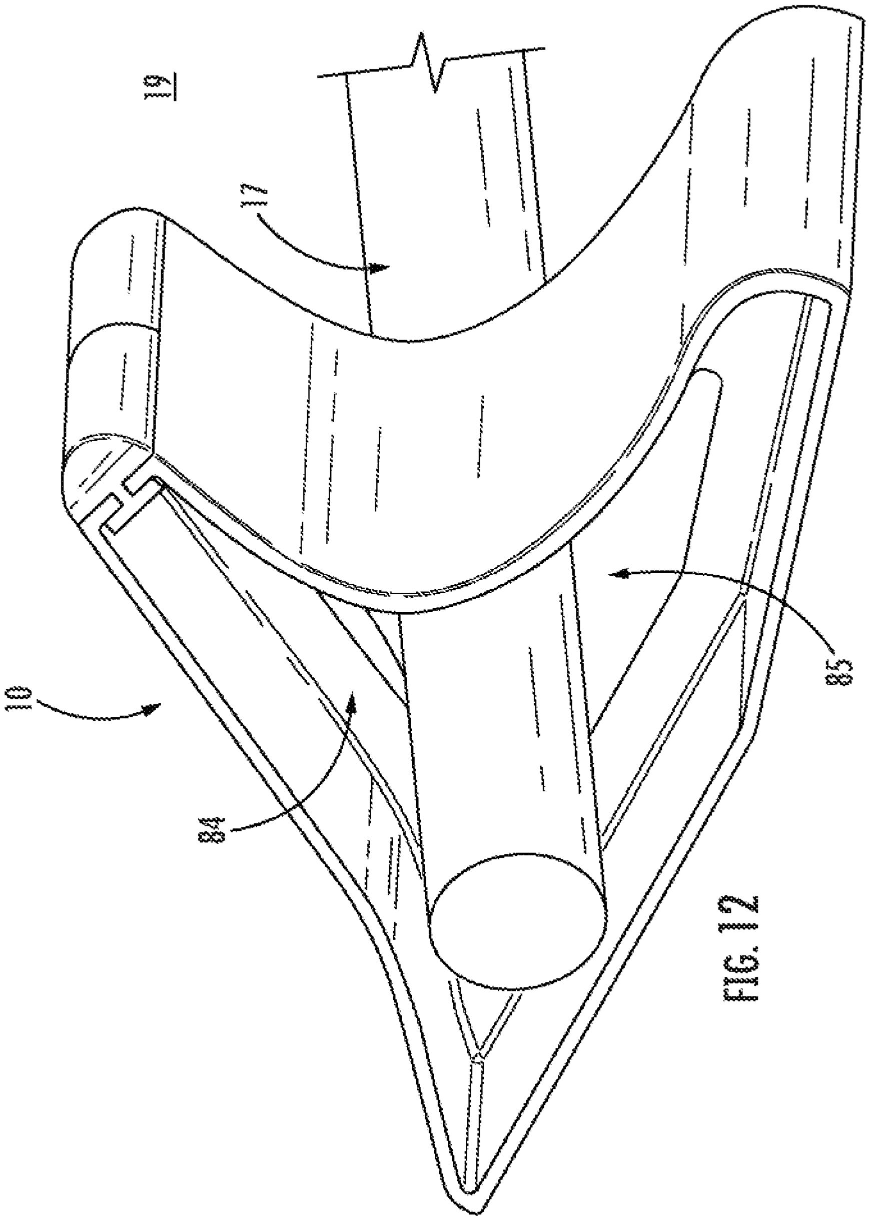
FIG. 12 illustrates the example muscle tension relief device shown in FIG. 1 hanging from a rod on a wall, in accordance with some embodiments discussed herein.

Returning to FIG. 1, in some embodiments, the muscle tension relief device 10 may include one or more mounting features, such as a hole 85. For example, with reference to FIG. 12, the muscle tension relief device 10 may hang via the hole 85. In the illustrated example, the muscle tension relief device 10 is hanging from a pole 17 extending from the wall 19 (e.g., the back wall rib 84 rests on the pole 17 that extends through the hole 85). In this regard, the muscle tension relief device 10 may be hung or mounted at home or in a gym. Although the illustrated embodiment includes a hole 85, other mounting features/options are contemplated (e.g., hanging on a hook, adding other mounting apertures, using adhesive, etc.).

Figure 13:
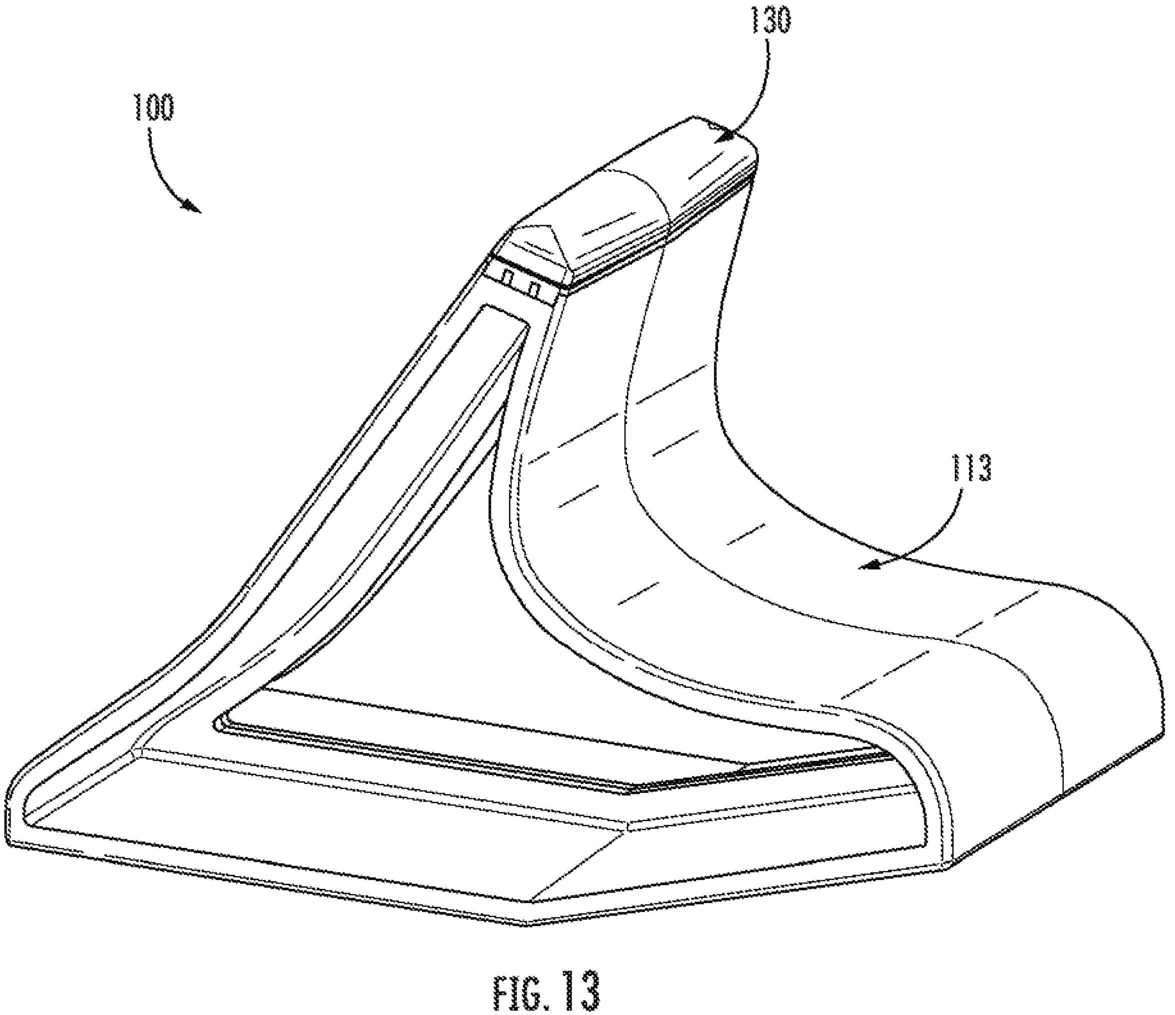
FIG. 13 shows a perspective view of another example muscle tension relief device, in accordance with some embodiments discussed herein.

FIG. 13 shows another example muscle tension relief device 100 that is similar to the muscle tension relief device 10 shown in FIG. 1. Notably, the muscle tension relief device 100 has a slightly different attachment for attaching the muscle engagement feature 130 to the body 113 of the muscle tension relief device 100.

Associated systems and methods for manufacturing example muscle tension relief devices described herein are also contemplated by some embodiments of the present invention.

CONCLUSION

Many modifications and other embodiments of the inventions set forth herein may come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the invention. In this regard, for example, different combinations of elements and/or functions than those explicitly described above are also contemplated within the scope of the invention. Although specific terms are employed herein, they are used in a generic and descriptive sense only and not for purposes of limitation.

The invention claimed is:

1. An apparatus for relieving muscle tension, the apparatus comprising:

a first base portion, wherein the first base portion comprises a flat surface extending in a first plane;

a second base portion, wherein the second base portion comprises a flat surface extending in a second plane, wherein a non-zero angle extends between the first plane and the second plane; and a muscle engagement feature extending generally upwardly relative to the first base portion, wherein the apparatus is configured to transition between a first position and a second position, wherein, when in the first position, the first base portion supports the apparatus on a surface with the second base portion lifted off the surface, and wherein, when in the second position, the second base portion supports the apparatus on the surface with the first base portion lifted off the surface.

2. The apparatus of claim 1, wherein the apparatus is configured to mimic a hand of a physical therapist to thereby provide a user of the apparatus with benefits achieved by the physical therapist without actually needing another person.

3. The apparatus of claim 1, wherein the apparatus is configured to transition from the first position to the second position based on a shift of weight of a user laying on the apparatus.

4. The apparatus of claim 3, wherein, when the muscle engagement feature is engaged with a lower abdomen of the user, while the apparatus transitions from the first position to the second position, the muscle engagement feature changes orientation such that the muscle engagement feature is configured to apply pressure on one of an iliacus muscle or a psoas muscle of the user.

5. The apparatus of claim 1, wherein the apparatus defines a front and a back, wherein the first base portion defines a front edge and a back edge, wherein the second base portion defines a front edge and a back edge, wherein the back edge of the first base portion defines the back of the apparatus and the front edge of the second base portion defines the front of the apparatus, and wherein the muscle engagement feature further extends in a direction toward the front of the apparatus.

6. The apparatus of claim 5, wherein the apparatus is configured to transition from a first position to a second position based on a shift of weight of a user laying on the apparatus, and wherein, when the apparatus is positioned beneath a lower abdomen of the user and oriented with the front of the apparatus toward a centerline of the user and with the muscle engagement feature engaged with the lower abdomen, while the apparatus transitions from the first position to the second position, the muscle engagement feature changes orientation to apply pressure on a psoas muscle of the user.

7. The apparatus of claim 6, wherein, when the apparatus is positioned beneath the lower abdomen of the user and oriented with the front of the apparatus away from the centerline of the user and with the muscle engagement feature engaged with the lower abdomen, the muscle engagement feature is configured to engage an iliacus muscle of the user.

8. The apparatus of claim 1, wherein the non-zero angle is between 1 degree and 30 degrees.

9. The apparatus of claim 1 further comprising a body extending from the first base portion and the second base portion to the muscle engagement feature.

10. The apparatus of claim 9, wherein the body defines a hole extending from a first side of the apparatus to a second side of the apparatus, and wherein the hole is configured to receive a structure therethrough for hanging the apparatus.

11. The apparatus of claim 9, wherein a portion of the body proximate the muscle engagement feature defines a width that is less than a width of the first base portion.

12. The apparatus of claim 9, wherein the body defines an integral structure along with the first base portion and the second base portion.

13. The apparatus of claim 12, wherein the body comprises a first material, wherein the muscle engagement feature comprises a second material, wherein the first material is different than the second material.

14. The apparatus of claim 13, wherein the second material is rubber.

15. An apparatus for relieving muscle tension, wherein the apparatus defines a front and a back, the apparatus comprising:

a first base portion;

a second base portion, wherein the second base portion extends in a direction upwardly relative to the first base portion and toward the front of the apparatus;

a muscle engagement feature extending in a direction generally upwardly relative to the first base portion and toward the front of the apparatus; and a body extending from the first base portion and the second base portion to the muscle engagement feature, wherein the apparatus is configured to transition between a first position and a second position, wherein, when in the first position, the first base portion supports the apparatus on a surface with the second base portion lifted off the surface, and wherein, when in the second position, the second base portion supports the apparatus on the surface with the first base portion lifted off the surface, wherein the apparatus is configured to mimic a hand of a physical therapist to thereby provide a user of the apparatus with benefits achieved by the physical therapist without actually needing another person.

16. An apparatus for relieving muscle tension, wherein the apparatus defines a front and a back, the apparatus comprising:

a first base portion defining a front edge and a back edge;

a second base portion defining a front edge and a back edge, wherein the back edge of the second base portion is adjacent the front edge of the first base portion, and wherein the second base portion extends upwardly from the first base portion and toward the front of the apparatus; and a muscle engagement feature extending in a direction generally upwardly relative to the first base portion and toward the front of the apparatus, wherein the apparatus is configured to transition between a first position and a second position, wherein, when in the first position, the first base portion supports the apparatus on a surface with the second base portion lifted off the surface, and wherein, when in the second position, the second base portion supports the apparatus on the surface with the first base portion lifted off the surface.

17. The apparatus of claim 16, wherein the apparatus is configured to transition from the first position to the second position based on a shift of weight of a user laying on the apparatus, and wherein, when the apparatus is positioned beneath a lower abdomen of the user and oriented with the front of the apparatus toward a centerline of the user and with the muscle engagement feature engaged with the lower abdomen, while the apparatus transitions from the first position to the second position, the muscle engagement feature changes orientation such that the muscle engagement feature is configured to apply pressure on a psoas muscle of the user.

18. The apparatus of claim 17, wherein, when the apparatus is positioned beneath the lower abdomen of the user and oriented with the front of the apparatus away from the centerline of the user and with the muscle engagement feature engaged with the lower abdomen, the muscle engagement feature is configured to engage an iliacus muscle of the user.

* * * * *